US012661302B2

(12) United States Patent (10) Patent No.: US 12,661,302 B2
Macor et al. (45) Date of Patent: Jun. 23, 2026

(54) HOME STOCK MANAGEMENT SYSTEM

(71) Applicant: Ares Trading S.A., Aubonne (CH)

(72) Inventors: Alessandro Macor; Wim Saelen, Coinsins (CH)

(73) Assignee: Ares Trading S.A., Aubonne (CH)

( * ) Notice: Subject to any disclaimer, the term of this patent is extended or adjusted under 35 U.S.C. 154(b) by 246 days.

(21) Appl. No.: 17/624,403

(22) PCT Filed: Jul. 5, 2019

(86) PCT No.: PCT/EP2019/068136
§ 371 (c)(1),
(2) Date: Jan. 3, 2022

(87) PCT Pub. No.: WO2021/004608
PCT Pub. Date: Jan. 14, 2021

(65) Prior Publication Data
US 2022/0354743 A1 Nov. 10, 2022

(51) Int. Cl.
*A61J 1/03* (2023.01)
*G06K 7/10* (2006.01)
(Continued)

(52) U.S. Cl.
CPC ............ *A61J 1/03* (2013.01); *G06K 7/10405* (2013.01); *G06Q 10/087* (2013.01); *G16H 20/10* (2018.01)

(58) Field of Classification Search
CPC .. G06Q 10/087; G16H 20/10; G06K 7/10405; A61J 1/03
(Continued)

(56) References Cited

U.S. PATENT DOCUMENTS 9,492,355 B2 * 11/2016 Ratnakar ................ G16H 20/13
9,734,294 B2 8/2017 MacDonald et al.
(Continued)

FOREIGN PATENT DOCUMENTS

CN 103020793 B 12/2016
EP 0915573 A2 5/1999
(Continued)

OTHER PUBLICATIONS

Eric Becker; SmartDrawer: RFID-Based Smart Medicine Drawer for Assistive Environments (Year: 2008).*
(Continued)

*Primary Examiner* — Ariel J Yu
*Assistant Examiner* — Denisse Y Ortiz Roman
(74) *Attorney, Agent, or Firm* — Carter, DeLuca & Farrell LLP

(57) ABSTRACT

Described herein is a home stock management system (1) for packaged items comprising a stationary data collection module (10) configured to wirelessly collect data from one or more packaged items (11) and to transmit the collected data to a processing module (12) wherein the packaged item(s) (11) include(s) a wireless tag (15), a processing module (12) for receiving, storing and processing the collected data from the collection module (10), and a notification means (13), wherein, the data collection module (10) is configured to collect data from the one or more packaged items (11) present in the home without user intervention. The processing module (12) is configured to process the collected data to determine status information and the notification means (13) is configured to communicate to one or more authorized users the status information. The home stock management system (1) can be used for the monitoring of consumable packaged items in the house or for monitor-
(Continued)

ing and managing the stock and use of medication in a patient home or residence.

19 Claims, 7 Drawing Sheets

(51) Int. Cl.
 G06Q 10/087 (2023.01)
 G16H 20/10 (2018.01)
(58) Field of Classification Search
 USPC ........................................................ 705/28
 See application file for complete search history.

(56) References Cited

U.S. PATENT DOCUMENTS

| | | | | |
|---|---|---|---|---|
| 2008/0040244 | A1* | 2/2008 | Ricciuti | .................. G06Q 10/08 705/28 |
| 2008/0054007 | A1 | 3/2008 | Mador | |
| 2008/0059228 | A1* | 3/2008 | Bossi | ..................... G16H 30/20 705/2 |
| 2009/0167531 | A1 | 7/2009 | Ferguson | |
| 2011/0148625 | A1 | 6/2011 | Velusamy | |
| 2012/0278228 | A1 | 11/2012 | Rubinstein | |
| 2014/0279291 | A1* | 9/2014 | Brosnan et al. | |
| 2016/0063286 | A1* | 3/2016 | Nikunen | ............ G06K 19/0716 340/10.34 |
| 2016/0371630 | A1* | 12/2016 | Jetcheva | ............ G06Q 30/0625 |
| 2020/0188234 | A1* | 6/2020 | Pietsch | ................. A61J 7/0454 |
| 2020/0364418 | A1 | 11/2020 | Gravelle | |

FOREIGN PATENT DOCUMENTS

| | | | | |
|---|---|---|---|---|
| JP | 2008506319 | A | 2/2008 | |
| JP | 2009100885 | A | 5/2009 | |
| JP | 2010035789 | A | 2/2010 | |
| JP | 2017511635 | A | 4/2017 | |
| WO | WO-2015132659 | A2 * | 9/2015 | ......... G06K 19/0723 |

OTHER PUBLICATIONS

International Search Report and Written Opinion of the International Searching Authority, dated Aug. 6, 2019, corresponding to counterpart International Application No. PCT/EP2019/068136; 13 total pages.
English translation of Japanese Office Action from application No. 2022-500107, Aug. 15, 2023, 34 pages.
European search report U.S. Appl. No. 19/737,517 dated Oct. 16, 2024.

* cited by examiner

(10) Stationary data collection module

(10) Data collection module

(13) Notification means

(15) Tags

(11) Tagged commodity items

(24) Power supply (battery)

(20,25) Communication and processing unit incl. memory

(26) Sensors (temperature, humidity, light intensity)

(28) Pill pocket with seal breakage detection

(29) Status indicator

(21) Tagged medication container (blister pack)

HOME STOCK MANAGEMENT SYSTEM

FIELD OF THE INVENTION

The present invention relates to a stock management system using an electronic communication element, such as for example a label or a tag. The communication element can be based on backscatter technology. More specifically, it relates to a home stock management system for consumables or medications and communication elements, such as for example labels or tags, based on radio frequency identification (RFID) technology attached to the consumables or medications for use in identifying, recognizing, and registering such consumables in a home environment.

BACKGROUND

Automation of the home environment has become more prevalent in today's homes. For example, certain electronic equipment in a home can be remotely operated. Frequently such remote management of in-home operated functions is enabled through the use of wireless or telecommunication communication methods, including the use of smart-phones to connect with the different types of equipment in the home. The use of such electronic devices provides additional functions in the management of home-based electronic equipment, such as whether a device or equipment is operating correctly. These developments have increased the ease of use of electronic devices in today's home environment. However, all such access to equipment requires intervention of the home owner to establish a connection between the remotely operated equipment and a communication device such as a smart phone. Moreover, such systems do not allow for stock management of items used in the home.

Stock management frequently involves tracking the presence and/or location of items in for example storage facilities. Typically, it is important to have accurate and up to date information on any stocked items in for example a storage facility or retail store in order to efficiently respond and monitor demand. Tracking availability and checking such information for any such items can be carried out manually but increasingly the use of wireless communication methods have either replaced or simplified the stock management systems employed in these environments.

In many cases such wireless communication involves the use of electronic tags, for example radio frequency (RF) tags, to track the presence of such stored items. However, such RF tags have only a limited range therefore requiring either that an individual, once in close proximity to the items, scans all present items with an appropriate reader, requiring a plurality of readers to be located throughout the monitored environment, or requiring a mobile reader movable throughout the monitored environment. Alternatively, an appropriate reader may be located at a strategic location within the monitored space for example at an entry/exit gate solely to track influx or efflux of the monitored items in the monitored space. This is not convenient for an individual in a home environment interested in a convenient method of monitoring the stock of consumable items in the home.

Similar to storage facilities and retail stores it is important for pharmacies and hospital pharmacies to accurately manage available medications. Not only available medications in general but also the tracking and managing the availability of all necessary items in a kit used by healthcare professionals, so called pharmacy kits is crucially important. As with the stored items in a storage facility, to such packaged medications or items in a pharmacy kit an electronic tag, such as a RF tag, can be affixed in order to wirelessly track its presence using an appropriate reader. The same drawbacks are observed here as with the storage facilities which require the user of the reader, or the reader itself, to be in close proximity to the tagged item or items.

Thus, one of the drawbacks of these stock management systems for use in a home to conveniently manage stock of consumable items is that due to the limited range of the RF tags a movable reader is required in order to sufficiently cover the entire home. Another drawback of many remote home operating systems using connected electronic equipment is the requirement for user intervention in either operating or initiating their use. For example, wireless communication using Bluetooth or Wi-Fi would require the resident of the home to perform an operation for pairing or other initiation of the communication. Therefore, there is a need for a convenient stock management system for use in a home to manage the presence and availability of connected consumables.

In addition, use of electronic tags on packaged items or consumables that are not conventional RFID tags would increase the cost of any system for home stock management. Such electronic home stock management system for consumables would need to be relatively cheap, versatile and have sufficient range to cover the entire home of the individual.

There is therefore a need for an affordable home stock management system which can without user interference effectively manage the availability or provide the user with sufficient information to manage the availability and status in the user's home of consumables, such as for example the user's medication.

BRIEF SUMMARY OF THE INVENTION

The present invention overcomes many of the afore mentioned drawbacks of stock management systems and provides an affordable and convenient solution for a home stock management system. Provided herein is a home stock management system for packaged items comprising: a) a stationary data collection module configured to wirelessly collect data from one or more packaged items and to transmit the collected data to a processing module wherein the packaged item(s) include(s) a wireless tag, b) a processing module for receiving, storing and processing the collected data from the collection module, and c) a notification means, wherein, the data collection module is configured to collect data from the one or more packaged items present in the home without human intervention; the processing module is configured to process the collected data to determine status information; and the notification means is configured to communicate with one or more authorized users the status information.

In another embodiment of the present invention there is provided a method of managing the stock of one or more packaged items, which packaged item(s) including(s) a wireless tag, in a home using a home stock management system.

In another embodiment of the present invention there is provided a medication stock management system in a home comprising the home stock management system wherein the packaged item is a medication container.

In another embodiment of the present invention there is provided a method of patient home management of a patient treatment plan comprising: determining the amounts of medication available for a patient treatment plan in a patient home; reminding the patient of an upcoming event relating to the medication as provided in a predetermined patient treatment plan; and notifying the patient that the available amount of medication according to the patient treatment plan is in need of being replenished or that the appropriate medication is present and ready for use, wherein the amounts of medication available for a patient treatment plan in a patient home are determined using the medication stock management system.

The present invention advantageously provides a convenient home stock management system which is affordable and convenient to use in a home environment. In addition, the stock management system can be used for the home stock management of medications for a patient and can advantageously manage and provide relevant status information to the patient and/or a patient's caregiver or other authorized individual relating to the patient's medication and its use in view of a treatment plan.

The above home stock management system and methods using such home stock management system or medication stock management system in a (patient) home in any of the embodiments are affordable using disposable wireless tags. These disposable wireless tags include a communication element which does not need any human intervention for initiating or activating communication within the stock management system described herein. As such the systems and methods described herein are not only affordable but also are easy to use. This is particularly important in a home setting for a stock management system considering that the resident(s) in the home are not always up to the task of establishing the proper initiation or activation of a communication of a packaged item that has a wireless tag with a central data processing module. For example, a patient using a medication home stock management system may be impaired to such extend as to not being able to take any steps to initiate a communication initiation of the packaged item having a wireless tag, such as pairing of such tag with any devices in the patient's home.

BRIEF DESCRIPTION OF THE DRAWINGS

The above-mentioned and other advantages and objects of this invention will become more apparent, and the invention itself will be better understood by reference to the following description of an embodiment of the invention together with the accompanying drawings, wherein.

Figure 1:
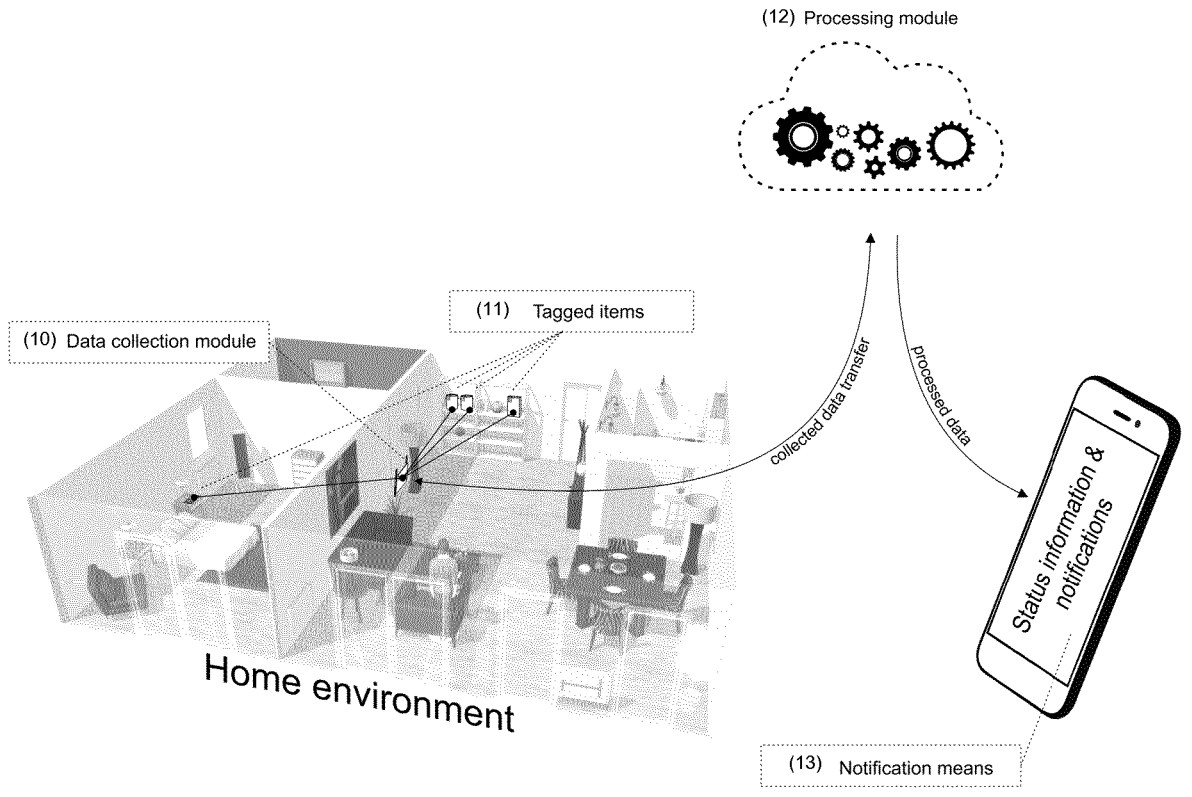
FIG. 1 is a representation of an embodiment of the home stock management system as placed in a home environment.
Figure 2A:
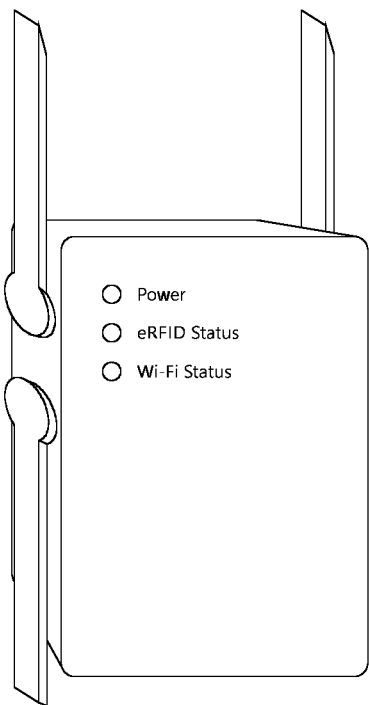
FIGS. 2A and B are representations of various types of data collection modules.
Figure 2B:
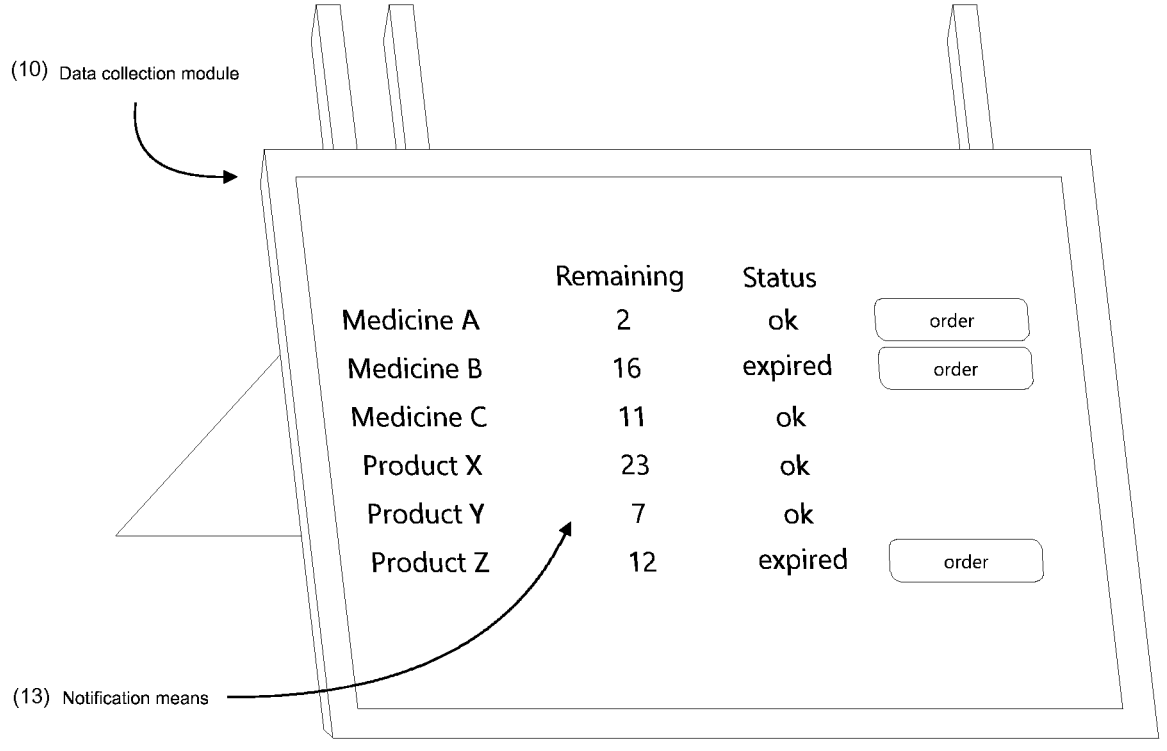

Corresponding reference characters indicate corresponding parts throughout the several views. Although the drawings represent an embodiment of the present invention, the drawings are not necessarily to scale, and certain features may be exaggerated or omitted in some of the drawings in order to better illustrate and explain the present invention.

DETAILED DESCRIPTION OF THE INVENTION

Embodiments of the inventive concept are described below with reference to the accompanying drawings where appropriate. These embodiments are presented as teaching examples and should not be construed to limit the scope of the inventive concept.

In one embodiment the present invention provides a home stock management system. In particular, as illustrated in FIG. 1 an embodiment of the home stock management system is shown wherein in a home environment (1) this system comprises a stationary data collection module (10), a processing module (12) and a notification means (13), wherein the data collection module (10) is configured to collect data from one or more packaged items (11) present in the home environment. The packaged items (11) include a wireless tag (15) (See for example FIG. 3A), which communicate with the data collection module (10) without human intervention. Such data collection module (10) is configured to wirelessly collect data from one or more of the packaged items (11) and to transmit the collected data to a processing module (12).

As described the data collection module (10) is configured to collect data from one or more packaged items (11) through wireless communication. In most other instances such wireless communication requires the operator, i.e. here the resident in the home environment, to initiate or activate (enable) wireless communication with each wireless communication element in the wireless tag (15). Often this requires several steps such as for example pairing of the wireless communication element (on a tagged packaged item) with the data collection module (10). However, in the present invention the wireless communication between the tagged packaged item(s) (11) and the data collection module (10) is without user intervention of the home resident. As such in the present invention the individual using the system, i.e. the resident of the home environment, does not have to initiate or activate (enable) any wireless communication or perform any active steps to initiate data transfer from any or all of the tagged item(s) (11) to the data collection module (10) or any subsequent data transfer, for example from the data collection module (10) to the processing module (12) or to the notification means (13). Accordingly, the wireless communication in the system is without user intervention.

Figure 3A:
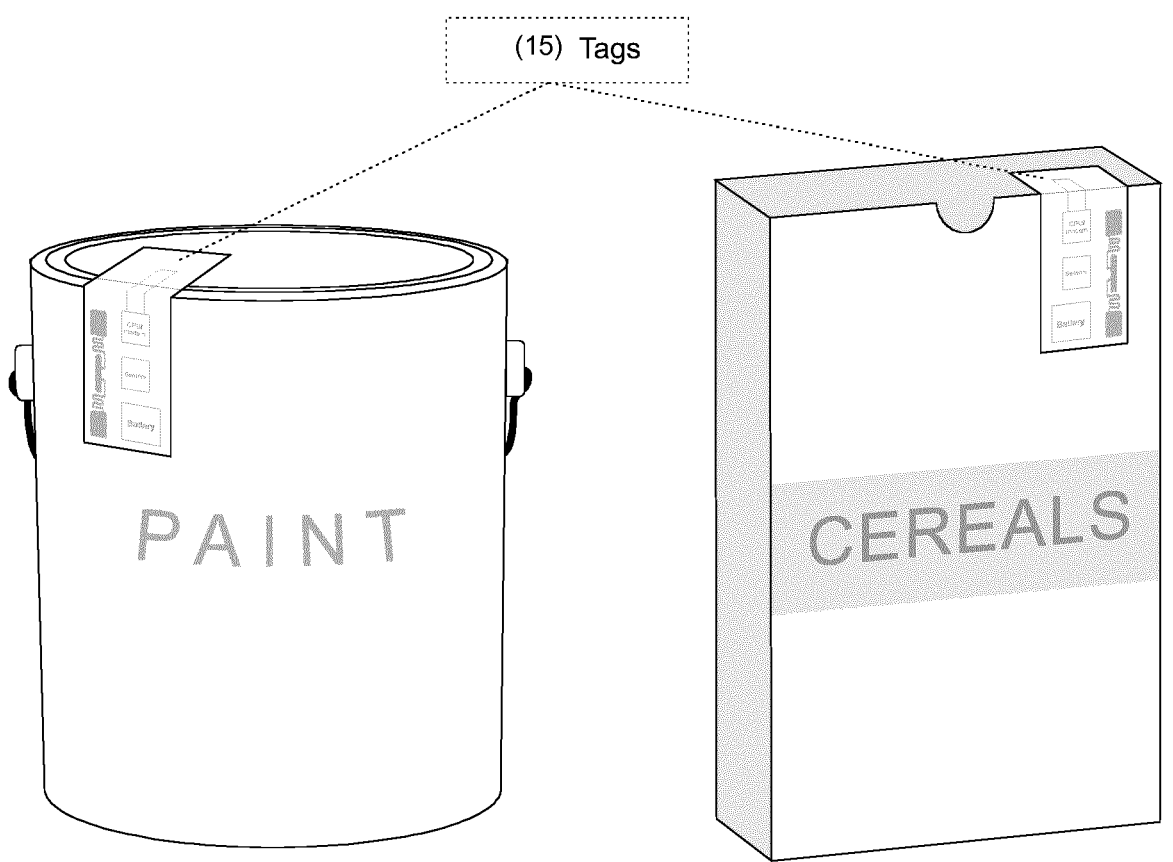
FIGS. 3A and B are representations of various types of packaged items which include a wireless tag.
Figure 3B:
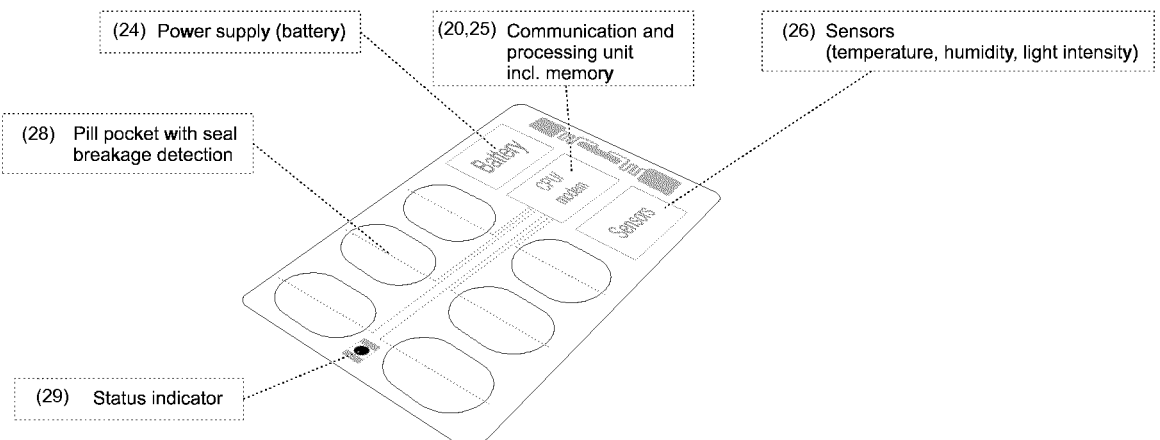

The wireless tag (15, 21) as shown for example in FIGS. 3A and 3B can include any wireless communication element (20) (as shown for example in FIG. 4) that can establish a wireless communication with the collection module (10). RF wireless communication provides for the possibility to establish a wireless connection without prior enabling or pairing of devices/elements. Unfortunately, most of the currently used conventional RFID technology can only operate at short range, at a range of less than about 2 m. This is too short of a range to be able to cover an entire home. A communication technology based on lost cost RF technology, for example as described in PCT/EP2018/085985 a "modified RFID technology", can establish accurate wireless communication at a longer range, for example up to about 100 m. In a preferred embodiment the wireless tag (15, 21) includes a communication element (20) having such modified RFID technology. Alternative low cost RF technology can further include Bluetooth low energy technology, ZigBee, or LoRa.

The communication element (20) having such modified RFID technology may be in the form of an electronic label, tag or module operably connected to a packaged item (11) and optionally connected with one or more sensors (26) (See for example FIG. 3B). Such operably connected communication element can be attached to or form an integral part of such packaged item (11) and can register any change to such packaged item. Such change being associated with the usage of what is contained in the packaged item or to a change in status such as for example temperature.

Figure 4A:
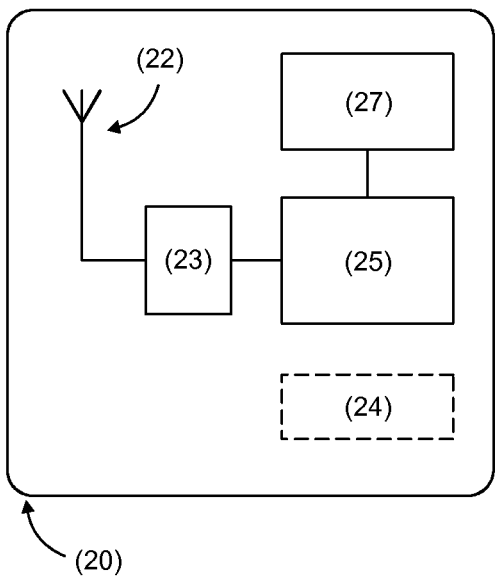
FIG. 4. Is a representation of a low cost based RF communication system wherein FIG. 4A schematically represents a communication element as part of the wireless tag and FIG. 4B schematically represents a configuration in the data collection module for communicating with the communication element.

As illustrated in FIG. 4A, an embodiment of such communication element (20) comprises a RF antenna (22), optionally a receiver (23) to receive data sent by the data collection module (10) (the 'downlink'), a modulator to modulate an incident RF signal and modulate data using backscatter onto the RF signal transmitted by the collection module (10) and a processing unit (25) for interpretation of data received from the collection module (10), and the generation of signals to modulate back to the data collection module (10). The processing unit (25) may comprise in an embodiment a direct sequence spread spectrum modulator for modulating data for transmission back to the data collection module (10) as a backscattered RF signal. The communication element (20) may also comprise a power source, used to power the communications and processing system. The communication element (20) may also comprise a memory (27), configured to store sensor data measurements by different sensors as described above and provide a connection for sensors and indicators. The memory (27) may be in the form of a printed memory and/or a silicon semiconductor-based memory, for example a memory chip or an integrated memory on the communication element.

In FIG. 3B an exemplary embodiment is shown for a medication container that has affixed to it a wireless tag (21), which wireless tag includes a communication element (20) as described above. In this embodiment the tagged medication container (21) is a blister pack. Such tagged medication container (21) includes a communication element (20), (including a processing unit (25) and a memory). Further included is a power supply (24) and one or more sensors (26). These sensors can obtain status information of the medication container (21) such as for example temperature, humidity or exposed light intensity. These sensors (26) can further include a sensor which detects changes in the physical shape (or tearing off) of the pill pocket seal (28). In addition, the tagged medication container (21) can include a status indicator (29), which may be a LED or a piezo buzzer, to provide feedback to the user/patient, for example to indicate that the medication container is ready or not ready for use.

Figure 4B:
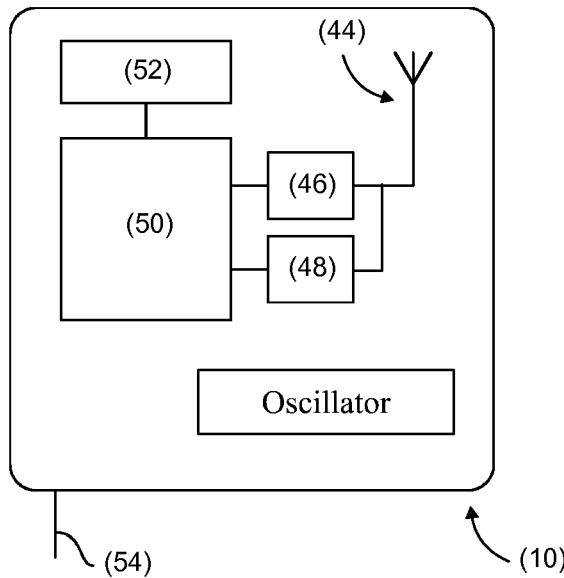

In combination with the communication element (20), in an embodiment of the present invention the data collection module (10) includes (as shown in FIG. 4B) at least one antenna (44), a transmitter (46) configured to transmit a RF signal through the antenna (44) to a communication element (20) and a receiver (48 configured to receive a backscattered RF signal from the communication element (20). A means for self-interference mitigation selected from one or more of, the presence of at least two RF antennas at the data collection module (10), analog carrier cancellation, digital carrier cancellation, and the use of a high pass filter, is further included to minimize interference between transmitted and received signals at the data collection module (10). In an embodiment, the data collection module (10) also comprises a processing unit (50), in particular for received signal de-modulation, processing and protocol handling. Where the signal received from the communication element (20) is modulated by a direct sequence spread spectrum modulator, the de-modulation can be a de-spreader.

The communication between the stationary data collection module (10) and the communication element (20) included in the wireless tag (11) can be achieved through an air interface protocol which uses continuous waves (CW) burst at the beginning of the transmission from the data collection module (10) to stimulate the powering of the communication element (20) as well as the generation of the internal clock signal within the communication element (20). The CW burst is followed by a command code transmitted as AM (Amplitude Modulation) on the carrier by the data collection module (10). The communication element (20) processes the command and responds by load modulating the antenna by applying ASK (Amplitude Shift Keying) or PSK (Phase Shift Keying) onto the incident CW signal from the data collection module (10) to generate the returned signal. In an advantageous embodiment, the communication element (20) may further comprise a Binary Amplitude Phase Shift Keying phase modulator or a Binary Phase Shift Keying phase modulator for phase modulation of the RF signal.

The processing module (12) can receive, store and process the collected data from the collection module (10). Processing of the collected data can be in the form of comparing the collected data, for example use data, with data stored in the processing module (12) to determine the status of the packaged items (11) present in the home or residence (1). The status includes for example remaining units left, expiration (or past expiration), temperature, etc. of the packaged items (11). The collected data can also be compared for example when the packaged item (11) is a medicament container (30) with a preset dosing regimen. Likewise, the collected data on a packaged item (11) which is a consumable can compare with preset or predetermined uses of the such consumable. The processing module (12) can initiate, based on the results of such comparisons, a feed back to the home owner or patient regarding the status of the packaged item(s) (11) through a notification means (13). It is understood that the processing module (12) can be any computerized processing unit and can be resident on for example the cloud or is an external server, external to the home environment. In certain embodiments of the present invention the processing module (12) is an integral part of the data collection module (10). As such the stationary data collection module (10) and the processing module (12) are a local (in home) data collection and processing hub.

The notification means (13) can be any user interface, for example a smart phone, a smart tablet, a personal computer, an integrated screen on the data collection module or an integrated display on the wireless tag (21) or on the package item (11). This notification means (13) therefore can be integrated with the data collection module (10) and the processing module (12) into a single stationary hub located with the home or residence (1). The notification means (13) can be not only sent a predetermined message to the user of the home stock management system but can also display the status information.

As described herein, status information includes for example presence, identification, expiration, authentication, amount present, usage, and storage condition information of the packaged item (11) in the home or residence (1).

Authorized users of the home stock management system can be regulated, and a preset group of authorized users can be identified for example at initial installment or initiation of the system and can be modified from time to time. Such authorized users are for example the home occupant and/or one or more users authorized by the home occupant to have access to the collected data and status information.

The home stock management system of the present invention determines the status of the packaged items (11) either at a regular time interval or can be prompted to determine the status of the packaged items (11) in the home or residence (1). The determination of the status any present packaged items (11) is carried out by the home stock management system of the present invention without human intervention. As such the home resident does not need to either initially pair or continuously pair the various items brought into the home or residence (1). The home stock management system records the presence (or absence) of any (new) packaged items (11) in the home or residence (1) at the expiration of the next time interval for scanning the home for packaged items (11). Such time interval is a regular time interval for data collection from every 5 sec to once a day. In an embodiment of the invention the regular time interval is from every 1 min to every 4 hours. Preferably, the regular time interval is from every hour to every 4 hours.

In addition, the wireless tag (15) can include information obtained from the one or more sensors (26) in communication with the communication element (20) or information loaded onto the tag through any other input means, for example using a computer interface to load data onto the wireless tag (15) at the time of the purchase or when the packaged item(s) (11) were obtained for example at the pharmacy. In certain embodiments the wireless communication tag (15) can be programmed with information stored in its memory (27) such as for example information where the packaged item was obtained (at the distribution point of the packaged items such as for example the pharmacy) and to which individual user, resident in the home, the packaged item should be assigned to. This can be particular of interest where the user is a resident in a home with multiple residents using the home stock management system (for example a patient in a home with multiple patients).

In embodiments wherein, the packaged item(s) (11) is/are medication containers the home stock management system is used as a patient medication stock management system. In such instances the home can be a residence wherein one or more patients reside, for example a patient's home or a retirement home, a clinic, a long-term care facility or a hospital. The medication stock management system in certain embodiments can also be used in a pharmacy. In any of such embodiment wherein the home stock management system is a medication stock management system, the packaged item (11) can be any medication container for example a blister pack, a vial, a syringe, a medication delivery device, or a pill bottle.

The collected data in such medication stock management system as described herein relates to data identifying the medication in the medication container and storage and use data of the medication. In certain embodiments, the processing module is further configured to compare the collected data relating to the medication with a predetermined medication dosing plan for a patient residing in the home who is prescribed and taking the medication to determine patient medication status information. The patient medication status information comprises one or more of presence, identification, expiration, authentication, frequency of usage, dose amounts used, storage conditions, and medication availability information. Further, the medication availability information comprises information on the availability of a medication to be taken by the patient according to the predetermined medication dosing plan.

In addition, the wireless tag (15) is programmable with medication specific information, such as prescription information, date of filling the prescription, counter-indications for the prescription at the pharmacy. As such, the wireless tag (15) also comprises identifying information selected from medication name, product code, dose amount, batch number, lot number, expiration date, stored temperature, relative humidity, production date, light intensity at storage and a combination thereof. In certain embodiments the wireless tag (15) is further interfaced with one or more sensors (26). These sensors (26) obtain relevant data regarding the status of the medication, such as for example temperature data.

In a further embodiment of the present invention the wireless tag (15) is further configured to receive and display status information of the medication. Such display of the status information is through an output means for example such as a LED light, an alpha-numeric or graphic display, or a piezo buzzer. Alternatively, the status information is received through an input means such as a button for user feedback or through a physical shape change of the packaged item. Such physical change of the packaged item can for example be a tearing off a strip or opening of the packaged item. The user can activate such input means to thereby provide status information or request a response relating to the status information of the medication.

EXAMPLE 1

An exemplary embodiment regarding medication home stock management includes the automatic monitoring of medication(s) in a patient's residence/home. A patient has been subscribed with a medication as part of his multi-dose treatment. The drug packaging contains the intelligent packaging solution as described herein, i.e. a medication container including a wireless tag. After having received a prescription from a health care provider, the patient visits a pharmacy to obtain a first few doses of the drug. The pharmacist scans the drug package and the patient's subscription, assigning the specific drug unit to the patient. The assignment and subscription information are shared with the online service provider. At the same time the authenticity and expiration information of the drug is being verified (the service provider keeps track of the uniqueness and status of each single drug unit). The service provider now knows which drug units have been supplied to the patient and when the patient is to take a dose of the drug. Optionally, during the scanning, the subscription information is also recorded into the intelligent packaging, i.e. stored in the memory of the wireless tag/communication element. Providing a secondary information exchange channel to the service provider in case no direct communication channel between pharmacy and service provider exists.

The patient enters the patient's home, which is equipped with the solution as described herein, with the medication(s) the patient obtained from the pharmacy. The stationary unit or hub (i.e. the stationary data collection module (10)) will detect presence of the medication(s) and share the unique ID of each single detected medication unit with the service provider. The service provider will be able to track the number of medication units still available at the patient's residence/home and, in case the service provider already received the information from the pharmacy, will be able to do a cross-check. Verifying if no drug units are missing and if the drug units are the ones assigned to the patient.

The stationary unit will continuously monitor the status of the detected medication units and providing this information to the processing module of the service provider which interfaces with the patient where applicable. Status information which is being monitored and provided services include:

> Environmental condition monitoring like temperature and relative humidity: when out of acceptable range, the service provider will notify the patient and suggest storing the medication(s) in a different place.

Expiration date check: in the unlikely event that a medication unit is about to expire, or if a recall operation is pending for this medication unit, the patient will be notified and asked to return the medication to the pharmacy for an exchange.

Presence detection: If the stationary can no longer detect the medication unit, it will notify the service provider which then can ask the patient for more clarification. Additionally, the service provider can notify the patient when he's running out of medication(s) or even arrange a new medication supply automatically.

State of use monitoring: The physical state change of the package indicating the potential use of the medication (s) will be detected by the stationary unit and recorded by the service provider. This state change is matched with the subscription information. Additionally, in case of a mismatch (no status change has been recorded while one was expected, a status change was detected while not expected), the service provider may ask the patient for more clarification. An overview of the recorded information is provided to the patient by the service provider and/or can automatically be shared with a health care provider.

In addition, the serviced provided can also include for example; asset tracking, anti-counterfeiting, data insights for the producer of the consumables or medications, adherence monitoring for the health care professional (HCP), and automated stock management and forecasting for distributors and pharmacies.

EXAMPLE 2

An exemplary embodiment regarding home stock management includes the monitoring of consumables in a residence/home. A home owner decides to cover a room in the house with a new cover of paint. After arriving at the paint store, the home owner realizes that there may be some remaining paint left from last time when a room in the home was painted. Instead of just buying more paint, the home owner uses his smart phone and connects with the home stock inventory service. The inventory service connects with the stationary data collection module which is installed in the home and instructs the it to do a complete scan. The hub reads the information of each detected intelligent package (i.e. a packaged item or consumable including a wireless tag) and returns it to the service provider. The service provider searches for and identifies the product ID which is associated with paint, checks in its database when the package was opened (this event was recorded the first time the paint was used) and verifies if the open container shelf live didn't exceed the advised shelf as in the instructions for use.

The home owner is then notified of the status for example the remaining paint was last used more than a year ago, so the stock inventory service advises to buy new paint. After returning home, the hub (i.e. the stationary data collection module) detects the new bucket of paint and informs the service provider to put it in the inventory. A few days later, the home owner decides to apply the first layer of paint and opens the bucket. The hub detects the opening event and instructs the service provider to record it. The home owner neglected to read the instructions for use which clearly state that for an optimal result, the second layer of paint shall be applied within 24 to 26 hours after the first layer in case of a relative humidity of 80%. The home owner the home stock management system included a reminder service. This reminder service tracks the time between the opening of the paint bucket—assuming the home owner started applying the first layer immediately after opening—and the Relative Humidity of in this case the bathroom which is a bit higher than 80% (on the condition that the bucket remains in the room being painted).

Eventually, about 25 hours after opening the bucket of paint (24 h+a correction relative to the RH), the home owner receives a reminder on his smart phone from the reminder service, suggesting for him to apply the next layer of paint.

While this invention has been shown and described as having preferred designs and features, the present invention may be modified within the spirit and scope of this disclosure. This application is therefore intended to cover any variations, uses or adaptations of the invention using its general principles. Further, this application is intended to cover such departures from the present disclosure as come within known or customary practice in the art to which this invention pertains.

The invention claimed is:

1. A home stock management system for packaged items, the home stock management system being a medication stock management system in a home wherein the packaged item is a medication container, the home stock management system comprising:

one or more processors; and a memory, including instructions stored thereon, which when executed by the one or more processors, cause the system to:

wirelessly collect and transmit data by a stationary hub from one or more packaged items, wherein the packaged item(s) include(s) a wireless tag, wherein the wireless tag comprises a communication element configured for powered spread spectrum backscatter RF wireless communication, wherein the communication element comprises a modulator configured to modulate the powered spread spectrum backscatter RF signal by modulation using binary phase shift keying or binary amplitude shift keying on the reflected powered spread spectrum backscatter RF signal, and wherein the data is collected from the one or more packaged items present in a home without user intervention;

receive and store the collected data from the stationary hub;

determine status information of the collected data; and communicate the status information to one or more authorized users, wherein the instructions, when executed by the one or more processors, further cause the system to, after receiving the collected data, compare the collected data with a predetermined medication dosing plan for a patient residing in the home taking the medication to determine patient medication status information, and alerting the patient and/or caregiver from any deviations from the predetermined medication dosing plan; and wherein the wireless tag further comprises a sensor for detecting a physical shape change of the medication container.

2. The home stock management system according to claim 1, wherein the instructions, when executed by the one or more processors, further cause the stationary hub to collect data at a regular time interval from the one or more packaged items present in the home.

3. The home stock management system according to claim 1, wherein the one or more authorized users is the home occupant and/or one or more users authorized by the home occupant to have access to the collected data and status information.

4. The home stock management system according to claim 1, wherein the status information comprises presence, identification, expiration, authentication, amount present, usage, and storage condition information of the packaged item in the home.

5. The home stock management system according to claim 1, wherein the instructions, when executed by the one or more processors, further cause the stationary hub to collect the data from the one or more packaged items present in the home through wireless communication.

6. The home stock management system according to claim 1, wherein the stationary hub further comprises a de-spreader for de-modulation of the spread spectrum back-scatter RF wireless communication prior to transmission of the data.

7. The home stock management system according claim 6, wherein the powered spread spectrum backscatter RF wireless communication is a powered direct sequence spread spectrum backscatter RF wireless communication.

8. The home stock management system according to claim 6, wherein the stationary hub further comprises a low phase noise signal source.

9. The home stock management system according to claim 6, wherein stationary hub further comprises one or more of a two antenna configuration, a high pass filter, and carrier cancellation self-interference mitigation selected from analog and digital.

10. The home stock management system according to claim 1, wherein the medication container is selected from a blister pack, a vial, a syringe, a medication delivery device and a pill bottle.

11. The home stock management system according to claim 1, wherein the wireless tag is interfaced with one or more user input and/or output means.

12. The home stock management system according to claim 1, wherein the wireless tag comprises identifying information selected from product code, batch number, lot number, expiration date, stored temperature, relative humidity, production date and a combination thereof.

13. The home stock management system according to claim 1, wherein the collected data comprises data identifying the medication in the medication container and storage and use data of the medication.

14. The home stock management system according to claim 1, wherein the patient medication status information comprises one or more of presence, identification, expiration, authentication, frequency of usage, dose amounts used, storage conditions, and medication availability information.

15. The home stock management system according to claim 1, wherein the wireless tag is programmable with medication specific information, such as prescription information, date of filling the prescription, counter-indications for the prescription at the pharmacy.

16. The home stock management system according to claim 1, wherein the wireless tag comprises identifying information selected from medication name, product code, dose amount, batch number, lot number, expiration date, stored temperature, relative humidity, production date and a combination thereof.

17. The home stock management system according to claim 1, wherein a physical state change of the medication container is detected by the stationary unit.

18. A method of patient home management of a patient treatment plan comprising:

a. determining the amounts of medication available for a patient treatment plan in a patient home;

b. reminding the patient for an upcoming event relating to the medication as provided in a predetermined patient treatment plan; and c. notifying the patient that the available amount of medication according to the patient treatment plan is in need of being replenished or that the appropriate medication is present and ready for use, wherein the amounts of medication available for a patient treatment plan in a patient home are determined using the home stock management system according to claim 1.

19. The home stock management system according to claim 1, wherein the stationary hub and the communication element communicate via an air interface protocol comprising:

using a continuous wave burst to power the communication element and generate an internal clock signal within the communication element;

transmitting a command code as amplitude modulation on a carrier by the stationary hub; and processing the command code by the communication element by applying amplitude shift keying or phase shift keying onto an incident continuous wave signal to generate a returned signal.

* * * * *